(12) United States Patent
Aslanyan et al.

(10) Patent No.: US 9,983,173 B2
(45) Date of Patent: May 29, 2018

(54) METHOD AND DEVICE FOR MULTI-SENSOR ELECTROMAGNETIC DEFECTOSCOPY OF WELL CASINGS

(71) Applicant: OBSCHESTVO S OGRANICHENNOY OTVETSTVENNOSTIU "MIKS", Kazan (RU)

(72) Inventors: Artur Mihailovich Aslanyan, Kazan (RU); Dmitry Aleksandrovich Davydov, Kazan (RU); Andrey Aleksandrovich Arbuzov, Kazan (RU); Anatoliy Nikolaevich Pestov, Tver (RU); Aleksandr Veniaminovich Klimochkin, Tver (RU); Pavel Aleksandrovich Yakonovskiy, Tver (RU); Vladimir Serafimovich Dolomanov, Tver (RU)

(73) Assignee: OBSCHESTVO S OGRANICHENNOY OTVETSTVENNOSTIU "MIKS", Kazan (RU)

( * ) Notice: Subject to any disclaimer, the term of this patent is extended or adjusted under 35 U.S.C. 154(b) by 88 days.

(21) Appl. No.: 14/786,340

(22) PCT Filed: Apr. 21, 2014

(86) PCT No.: PCT/RU2014/000291
§ 371 (c)(1),
(2) Date: Oct. 22, 2015

(87) PCT Pub. No.: WO2014/175785
PCT Pub. Date: Oct. 30, 2014

(65) Prior Publication Data
US 2016/0061776 A1 Mar. 3, 2016

(30) Foreign Application Priority Data

Apr. 22, 2013 (EA) .................................. 2013000058

(51) Int. Cl.
*G01N 27/90* (2006.01)
*E21B 47/00* (2012.01)
(Continued)

(52) U.S. Cl.
CPC ....... *G01N 27/902* (2013.01); *E21B 17/1028* (2013.01); *E21B 47/00* (2013.01);
(Continued)

(58) Field of Classification Search
CPC ...... E21B 47/00; E21B 17/1028; E21B 47/01; G01N 27/902; G01N 27/904; G01V 3/28
(Continued)

(56) References Cited

U.S. PATENT DOCUMENTS 2,717,039 A * 9/1955 Gieske ................ E21B 47/0905
166/63
3,317,824 A * 5/1967 Wood .................... E21B 47/082
324/221
(Continued)

FOREIGN PATENT DOCUMENTS

RU 2215143 10/2003
SU 972895 3/1992

OTHER PUBLICATIONS

GE Oil & Gas—Magnetic Thickness Tool.

*Primary Examiner* — Jay Patidar
(74) *Attorney, Agent, or Firm* — Boyle Fredrickson S.C.

(57) ABSTRACT

A group of inventions related to geophysical well logging, in particular to magnetic imaging defectoscopy of well casings including magnetized ones, that can be used to identify and classify defects in production and intermediate casing and
(Continued)

tubing strings in oil and gas wells. An electromagnetic multi-sensor defectoscope for surveying casing pipes containing a source of the electromagnetic field in the form of a central exciter coil designed to transmit current pulses from a current pulse generator, a system of measuring elements placed on bow springs to be forced against the inner surface of a casing pipe, and a unit for signal recording, control and data processing connected to the system of measuring elements through communication lines. A method of multi-sensor electromagnetic defectoscopy for surveying casing pipes.

12 Claims, 3 Drawing Sheets

(51) Int. Cl.
*E21B 47/01* (2012.01)
*E21B 17/10* (2006.01)
*G01V 3/28* (2006.01)

(52) U.S. Cl.
CPC ........... *E21B 47/01* (2013.01); *G01N 27/904* (2013.01); *G01V 3/28* (2013.01)

(58) Field of Classification Search
USPC .................................................. 324/220–221
See application file for complete search history.

(56) References Cited

U.S. PATENT DOCUMENTS 4,292,589 A * 9/1981 Bonner ................. E21B 47/082
324/221
5,233,297 A 8/1993 Lara
7,960,969 B2 6/2011 Mouget et al.

* cited by examiner

METHOD AND DEVICE FOR MULTI-SENSOR ELECTROMAGNETIC DEFECTOSCOPY OF WELL CASINGS

TECHNICAL FIELD

A group of inventions related to geophysical well logging, in particular to magnetic imaging defectoscopy of well casings including magnetised ones, that can be used to identify and classify defects in production and intermediate casing and tubing strings in oil and gas wells.

BACKGROUND ART

There is a known electromagnetic module, MTT of Sondex, to identify defects in tubing strings (Magnetic thickness tools-MTT. Leading Oilfield Technology. *Sondex*, p. 10, http://www.sondex.com). The MTT consists of one exciter coil and 12 miniature magnetic sensors, mounted on the inside of bow springs. The generator operates at three frequencies. The signal amplitude and phase at the pick-up coil depend on the amount of metal surrounding a sensor.

The drawback of this known logging tool is that, while it can identify defects in one tubing string or an interval of the casing string after withdrawal from tubing, it cannot distinguish between defects on the inner and outer sides of a string. Moreover, this logging tool cannot see hole-type defects less than 15 mm in diameter.

There is a known device that can identify defects and perforations in pipe strings. The downhole electromagnetic defectoscope includes a housing, an exciter coil with its magnetic axis being aligned with the tool's axis, and a pick-up coil with its magnetic axis being perpendicular to the tool's axis (RF patent No. 2215143, published 27 Oct. 2003, E21B49/00, G01N27/90). In this known device, an alternating current is fed into the exciter coil to generate loop eddy currents in the surrounding steel pipe, and those, in turn, induce an EMF in pick-up coils. As the pick-up coils pass by defects in the pipe string, characteristic changes in the magnetic field are observed.

The drawback of this device is its inability to distinguish between defects on the inner and outer surfaces of a pipe. Moreover, a defect can be detected if it is in close proximity to the pick-up coil.

There is a method and a device to inspect objects, including pipes, using moving sensors, known from the U.S. Pat. No. 5,233,297 (Atlantic Richfield Company, published 3 Aug. 1993, IPC G01N 27/72, G01N 27/82, G01R 33/12, G01B 7/10). The device contains an active region with a transmitting element and at least one pick-up element (sensor). The transmitting element is connected to a pulse current source that generates a magnetic field and is, in turn, connected to a microcontroller. The active region is in close proximity to the walls of a surveyed object, so that the sensors touch its walls and are equidistant from one another. The active region moves along the object and the transmitting element induces a pulsed current in the object's walls. The sensors detect the currents induced in the object's walls after every current pulse and transmit the received signals for processing. Then, these data are interpreted to determine the thickness of the object. The object's wall thickness is determined by comparing the received signal with the reference one that is generated using an object of known thickness. The drawback of the device is that it measures only local pipe wall thicknesses.

There is a device for downhole casing control known from the Author's Certificate No. 972895, published on 23 Mar. 1992, G01 N 27/87. The device contains numerous sensors located on the circumference of a casing string in one plane. The sensors consist of cores and magnetic paths separated by a non-magnetic spacer or air clearance, and of coils with outputs. The magnetic flux through defects is higher than that through undamaged areas, which is the main criterion for defect detection.

The drawback of this device is that it can be used to detect only large defects. Moreover, its design requires a large size of the device. Therefore, it can only be used in large-diameter pipes, for instance, in gas pipelines.

There is an electromagnetic method, known from the U.S. Pat. No. 7,960,969, Schlumberger Technology Corp., published on 14 Jun. 2011, IPC E21B 47/08, for the electromagnetic measurement of the physical properties of pipes using a device containing multiple transmitting and pick-up coils connected so that they form multiple measuring devices designed to be placed and moved in a pipe. Physical properties are measured at multiple positions in the pipe. The essence of this known method is as follows. A magnetic field is generated in the object under study by current pulses through an exciter coil. The response of this field is recorded in the tool's memory as the time dependence of the EMF of output signals from uncompensated sensors placed equidistantly from one another on the cross-section circumference of the casing pipe under study. Then, the recorded signals are processed to identify defects on the cross-section circumference of the casing pipe under study.

This solution is the closest in its technical essence to the proposed group of inventions. The main drawback of this known solution is that the magnetic field response is measured by a measuring device that cannot measure the response signals of the secondary electromagnetic field if most response signals of the primary electromagnetic field are simultaneously compensated, because it contains, among others, uncompensated sensors only. This narrows the dynamic range of the magnetic field's response signal for small defects, which makes their detection impossible and decreases the resolution.

Thus, state-of-the-art analysis shows that the known technical solutions cannot ensure detection of small defects, such as 3-5-mm holes, in casing strings. Moreover, small defects, such as holes larger than 15 mm in diameter, can be detected if they are in close proximity to the sensor.

DISCLOSURE OF INVENTION

The general objective of the group of inventions and the required technical result to be achieved through their use is the development of a new method and a tool for electromagnetic defectoscopy of casing pipes as well as enhancing the informativeness and resolution of measurements and increasing the sensitivity to small defects in casing pipes. The aim of the group of inventions and the required technical result are achieved due to the fact that the electromagnetic multi-sensor defectoscope for surveying casing pipes contains a source of the electromagnetic field in the form of a central exciter coil designed to transmit current pulses from a pulsed current generator, a system of measuring elements placed on bow springs to be forced against the inner surface of a casing pipe, and a unit for signal recording, control and data processing connected to the system of measuring elements through communication lines, and that, according to the invention, the system of measuring elements designed to record signals proportional to the longitudinal component of the electromagnetic field consists of at least three compensated sensors, each equidistant from one another on the circumference of the cross-section of a casing pipe so that they ensure reliable detection of defects within its surveyed section. Each compensated sensor contains two co-axial pick-up coils with magnetic moments that have equal absolute values and opposite signs, one of them at the same time being an uncompensated sensor, and with their magnetic axes being parallel to the central longitudinal axis of the defectoscope.

Each compensated sensor is placed near the inner surface of a casing pipe and symmetrically to the central exciter coil.

The communication lines of the sensors with a signal recording, control and data processing unit are placed in flexible, highly temperature and pressure resistant and hydrogen-sulphide resistant protective housings, preferably with spiral winding.

The aim of the group of inventions and the required technical result are also achieved due to the fact that the method of electromagnetic multi-sensor defectoscopy for surveying casing pipes, in which an electromagnetic field is generated within the surveyed section of a casing pipe by current pulses, response signals of this electromagnetic field are measured in the intervals between excitation pulses using a system of measuring elements, the signals are transmitted into a signal recording, control and data processing unit, and that, according to the invention, mainly the response signals of the secondary electromagnetic field are measured, and most response signals of the primary electromagnetic field are compensated, while recording the time dependence of the output EMF of the signal of the system of measuring elements.

The response signals of the electromagnetic field are measured by at least three compensated sensors, each containing two co-axial pick-up coils with magnetic moments that have equal absolute values and opposite signs.

The measured parameter is the differential EMF, induced in the pick-up coils of each compensated sensor, and the variation of the maximum value and sign of the time dependence of the compensated sensor's output EMF is used as one of the indications of defects in a casing pipe.

The distinctive feature of the proposed group of inventions is a new method of multi-sensor electromagnetic defectoscopy to measure, primarily, the response signals of the secondary electromagnetic field, while compensating most response signals of the primary electromagnetic field, and a new multi-sensor electromagnetic defectoscope, including a redesigned system of measuring elements allowing the measurement of mainly response signals of the secondary electromagnetic field generated by an inductive exciter coil excited with periodic current pulses of preset duration. The system of measuring elements records signals that are proportional to the longitudinal component of the electromagnetic field. This enhances the informativeness of measurements and, at the same time, increase the sensitivity to small defects. Additionally, the redesigned system of measuring elements contains a combination of compensated and uncompensated sensors, which enhances the resolution and allows the detection of magnetic field inhomogeneities caused by even small defects (for instance, a hole larger than 3 mm in diameter) in metal casing strings, including highly magnetised ones. Additionally, the redesigned system of measuring elements allows, after the recording of signals and their processing (measured data processing), the distinguishing between defects on the inner and outer pipe surfaces, which increases the informativeness.

BRIEF DESCRIPTION OF DRAWINGS

The essence of the group of inventions is illustrated by drawings.

BEST MODE FOR CARRYING OUT THE INVENTION

Figure 1:
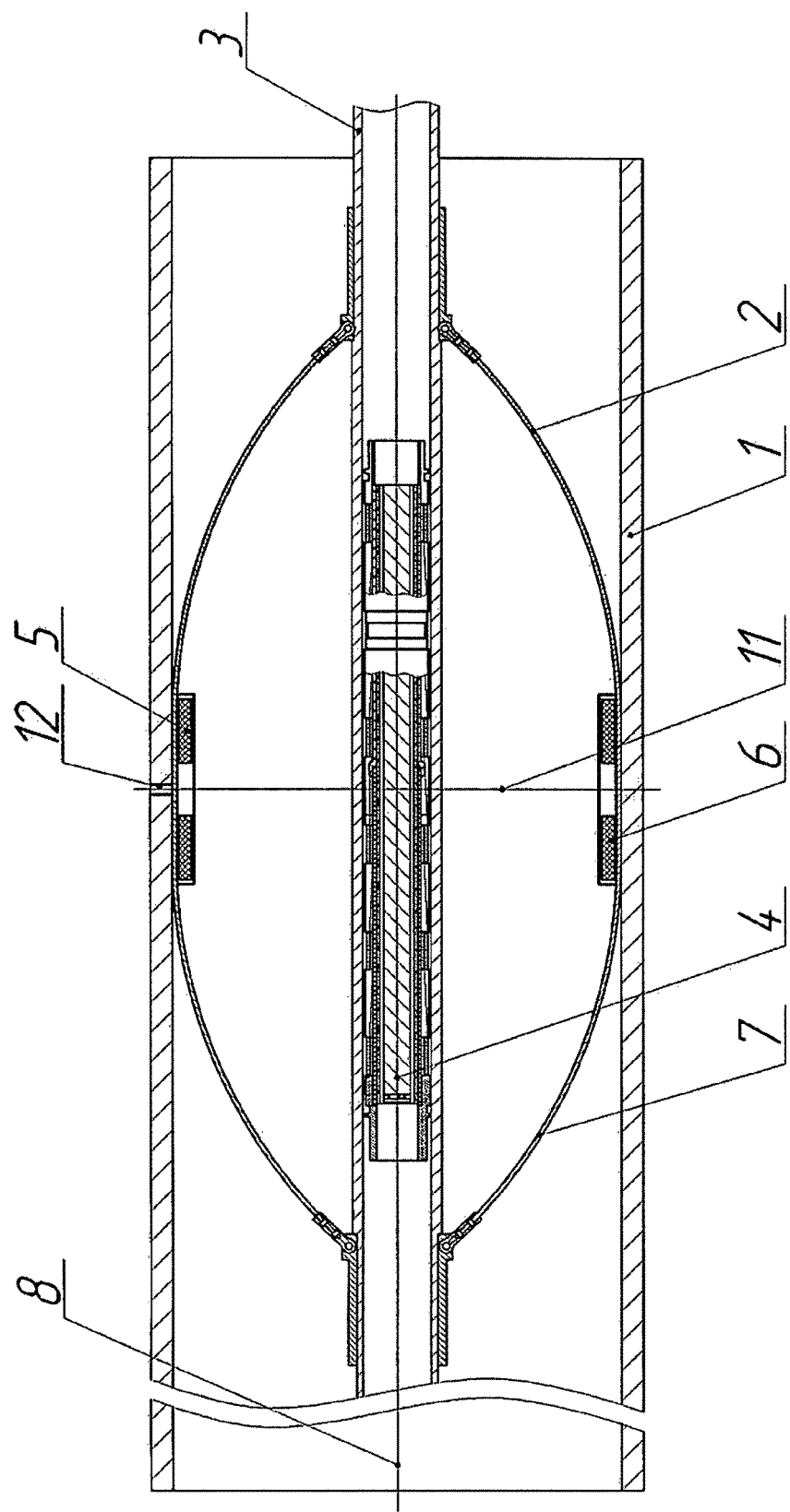
FIG. 1 shows a longitudinal cross-section of an electromagnetic multi-sensor defectoscope placed in a casing string.
Figure 3:
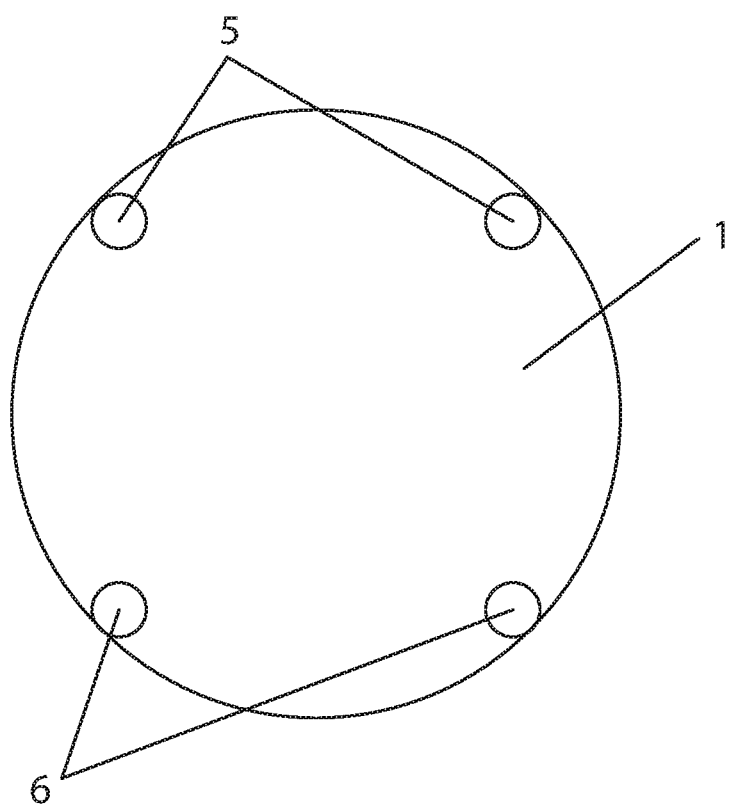
FIG. 3 shows a diagram of sensors of the defectoscope being equidistant from one another along a circumference of a cross-section of pipe in one plane.

Casing Pipe 1 accommodates Electromagnetic Defectoscope 2 with Housing 3 containing the longitudinal Inductive Exciter Coil 4 of the tool, co-axial with Pipe 1, and four Compensated Sensors 5 and 6 contained in a housing (not shown in the drawings) and placed on the inner side of Non-Magnetic Bow Springs 7 ensuring that Sensors 5 and 6 are forced against the inner surface of Casing Pipe 1 (FIG. 1). Sensors 5 and 6 are placed on the inner surface of Bow Springs 7 to minimize their wear during operation due to no friction (abrasion) between them and the wall of Casing Pipe 1. Sensors 5 and 6 are equidistant from one another along the circumference of the cross-section of Pipe 1 in one plane (FIG. 3). Because FIG. 1 is a cross-section of Defectoscope 2 in Pipe 1, only two sensors, 5 and 6, are seen in it. Actually, the number of sensors can be larger but not less than three. The number of sensors cannot be less than three to locate defects on the circumference of the cross-section of Pipe 1 in one plane with enough detail. The number of Sensors 5 and 6 depends on the diameter of the surveyed Pipe 1. The larger the pipe diameter, the larger number of sensors must be in the defectoscope to ensure a sufficiently high probability of finding defects in the surveyed casing pipe section.

The longitudinal inductive Exciter Coil 4 is aligned along the central Longitudinal Axis 8 of Defectoscope 2. The magnetic axis of the inductive Exciter Coil 4 is directed along the logging tool. The compensated Sensors 5 and 6 are placed right in the middle of Exciter Coil 4 for their best compensation in a solid-wall (defect-free) casing pipe.

Figure 2:
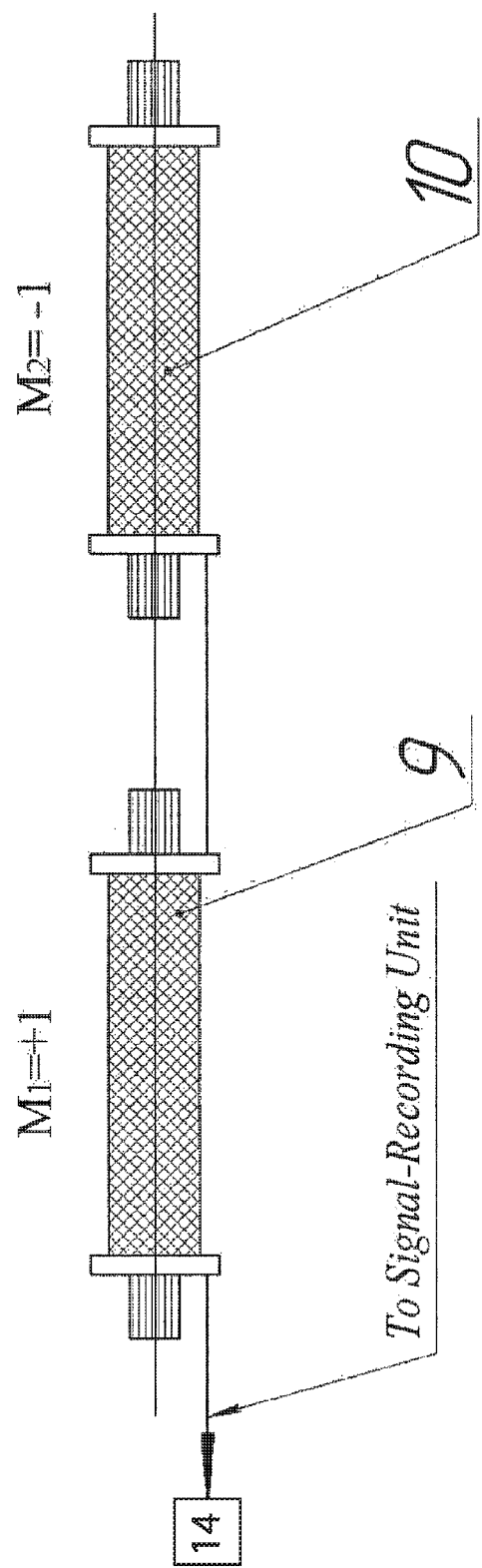
FIG. 2 shows a layout of pick-up coils of a compensated sensor, where $M_1$ and $M_2$ are relative magnetic moments.

Each of Sensors 5 and 6 contains two co-axial Pick-Up Coils 9 and 10 (FIG. 2). One of Coils 9 and 10 is, at the same time, an uncompensated sensor for additional determination of thickness distribution along the circumference of the cross-section of Pipe 1 in one plane. Because Compensated Sensors 5 and 6 are placed right in the middle of Exciter Coil 4, a pair of coils in each of them is precisely compensated in the solid-wall (defect-free) Casing Pipe 1 (FIG. 1; also shows Coils' Symmetry Axis 11). Coils 9 and 10 are connected in anti-phase mode, i.e. with magnetic moments being equal in value but opposite in sign, for precise compensation of the primary magnetic field in the solid-wall (defect-free) Casing Pipe 1. The magnetic axes of Coils 9 and 10 are parallel to Central Axis 8 of Defectoscope 2, which allows measuring the longitudinal component of the response of the secondary magnetic field. Coils 9 and 10 are compensated so that Sensors 5 and 6 in the absence of defects induce the minimum EMF at the output of the measuring circuit, while the sensors are additionally decompensated near Defect 12, which substantially changes the output EMF. This allows the detection of magnetic field inhomogeneities caused by even small defects (for instance, holes larger than 3 mm in diameter) in metal casing strings, including highly magnetised ones. The parameters characterising the size and geometry of defects are the amplitude and shape of the time dependence of the output EMF of the sensor's signal (response from a pipe with defects). It should be noted that the active regions of each of Sensors 5 and 6 are located near the butt ends of their coils and near the butt ends of the core of Exciter Coil 4.

Sensors 5 and 6 are connected to the signal recording, control and data processing unit 14 (FIG. 2) through communication lines. The communication lines of Sensors 5 and 6 with the signal recording, control and data processing unit 14 are placed in flexible, highly temperature and pressure resistant and hydrogen-sulphide resistant protective housings, both straight and with spiral winding (not shown in the drawings). These requirements are defined by the defectoscope's operating conditions.

The device operates as follows.

Electromagnetic Defectoscope 2 is placed in Casing Pipe 1. Periodic current pulses of preset duration are passed through Exciter Coil 4 from a current pulse generator (not shown in the drawings). The differential EMF induced in Pick-Up Coils 9 and 10 of each of Sensors 5 and 6 by eddy currents generated by electromagnetic field decay in the surveyed casing due to magnetization current pulses of the axial Exciter Coil 4 is measured in the intervals between excitation pulses. It should be noted that the signals of the secondary electromagnetic held are measured, while the signals of the primary electromagnetic field are compensated due to equal magnetic moments of the coils of the compensated Sensors 5 and 6. Signals received from Sensors 5 and 6 are transmitted to the signal recording, control and data processing unit 14, in which the variation of the maximum value and sign of the time dependence of the compensated sensor's output EMF of a signal of each of Sensors 5 and 6 is an indication of Defect 12 in Casing Pipe 1. During operation, Defectoscope 2 moves along Pipe 1. The passage of Defectoscope 2 from one diameter of Pipe 1 into another does not prevent or degrade measurements due to non-magnetic Bow Springs 7 of special design allowing the adjustment of their deflection depending on the diameter of Pipe 1 and due to the placement of Sensors 5 and 6 on the inner surface of Bow Springs 7.

Thus, the redesigned system of measuring elements can measure the signals of the secondary electromagnetic field generated by an inductive exciter coil, while recording signals that are proportional to the longitudinal component of the electromagnetic field. Moreover, the redesigned system of measuring elements contains a combination of compensated and uncompensated sensors and allows the detection of magnetic field inhomogeneities caused by even small defects (for instance, a hole larger than 3 mm in diameter) in metal casing strings, including highly magnetised ones, which, together with the above-mentioned distinctive features, enhances the resolution and informativeness of measurements while increasing the sensitivity to small defects in casing pipes, i.e. ensures achieving the claimed technical result. Additionally, the redesigned system of measuring elements allows, after proper processing of measured data, the distinguishing between defects on the inner and outer pipe surfaces, which also increases the informativeness.

The claimed group of inventions for the method and device of multi-sensor electromagnetic defectoscopy of well casing strings can, in both general and particular cases, be implemented using known materials, components and modules employed for electromagnetic defectoscopy of casing strings.

Specifically, pressure-resistant housings made of non-magnetic low-conductivity material—for example VT3-1 titanium or BRB2 bronze—can be used as Housing 3 and housings for Sensors 5 and 6.

The device for multi-sensor electromagnetic defectoscopy of well casing strings may additionally contain an adapter for reading-out information, an independent power supply and other components.

The device for multi-sensor electromagnetic defectoscopy of well casings can also be used for defectoscopy of metal pipes in other systems, such as gas lines, water lines, etc.

Possible implementations of this group of inventions are not limited to the above-described options but, on the contrary, comprise various modifications and alterations within the scope and spirit of the patent claim.

The invention claimed is:

1. An electromagnetic multi-sensor defectoscope for surveying a casing pipe, the defectoscope comprising: a central exciter coil configured to produce an electromagnetic field according to current pulses from a current pulse generator, a system of measuring elements placed on bow springs to be forced against the inner surface of the casing pipe, and a unit for signal recording connected to the system of measuring elements through communication lines, wherein the system of measuring elements, arranged to capture signals proportional to a longitudinal component of the electromagnetic field defined along a central longitudinal axis of the defectoscope, comprises at least three compensated sensors, each equidistant from one another along the circumference of the casing pipe so that each sensor ensures reliable detection of defects within its surveyed section, wherein each compensated sensor contains two co-axial pick-up coils with magnetic moments that have equal absolute values and opposite signs.

2. The electromagnetic multi-sensor defectoscope according to claim 1, wherein one of the two co-axial pick-up coils of each compensated sensor is further configured as an uncompensated sensor connected to the unit.

3. The electromagnetic multi-sensor defectoscope according to claim 1, wherein the magnetic axes of the two co-axial pick-up coils of each compensated sensor are parallel to the central longitudinal axis of the defectoscope.

4. The electromagnetic multi-sensor defectoscope according to claim 1, wherein each compensated sensor is placed near the inner surface of the casing pipe and symmetrically to the central exciter coil.

5. The electromagnetic multi-sensor defectoscope according to claim 1, wherein the communication lines of the sensors with the signal recording unit are placed in flexible, highly temperature and pressure resistant and hydrogen-sulphide resistant protective housings.

6. The electromagnetic multi-sensor defectoscope according to claim 5, wherein the signal recording further provides control and data processing.

7. The electromagnetic multi-sensor defectoscope according to claim 1, wherein the system of measuring elements is placed on an inner surface of the bow springs.

8. A method of multi-sensor electromagnetic defectoscopy for surveying casing pipe, the method comprising: generating a primary electromagnetic field within a surveyed section of the casing pipe by current pulses, measuring response signals of the primary electromagnetic field in intervals between excitation pulses using a system of measuring elements, and transmitting the response signals into a signal recording unit, wherein the response signals are compensated from the system of measuring elements by using compensated sensors which each contain two co-axial pick-up coils with magnetic moments that have equal absolute values and opposite signs.

9. The method of electromagnetic multi-sensor defectoscopy according to claim 8, wherein the response signals of the electromagnetic field are measured by at least three compensated sensors.

10. The method of electromagnetic defectoscopy according to claim 9, wherein a differential EMF, induced in the pick-up coils of each compensated sensor, is measured.

11. The method of multi-sensor electromagnetic defectoscopy according to claim 10, wherein the variation of the maximum value and sign of a time dependence of each compensated sensor's output is used as an indication of a defects in the casing pipe.

12. The method of multi-sensor electromagnetic defectoscopy according to claim 9, wherein one of the two co-axial pick-up coils of each compensated sensor is further configured as an uncompensated sensor connected to the unit.

* * * * *